United States Patent
Schneider et al.

(10) Patent No.: US 10,004,523 B2
(45) Date of Patent: Jun. 26, 2018

(54) ENDOSCOPIC INSTRUMENT, AND SHAFT FOR AN ENDOSCOPIC INSTRUMENT

(71) Applicant: Karl Storz SE & Co. KG, Tuttlingen (DE)

(72) Inventors: Sven Schneider, Tuttlingen (DE); Tobias Unger, Tuttlingen (DE)

(73) Assignee: Karl Storz SE & Co. KG, Tuttlingen (DE)

( * ) Notice: Subject to any disclaimer, the term of this patent is extended or adjusted under 35 U.S.C. 154(b) by 44 days.

(21) Appl. No.: 14/185,622

(22) Filed: Feb. 20, 2014

(65) Prior Publication Data
US 2014/0236147 A1   Aug. 21, 2014

(30) Foreign Application Priority Data
Feb. 20, 2013   (DE) ........................ 10 2013 101 651

(51) Int. Cl.
| | | |
|---|---|---|
| A61B 18/18 | (2006.01) | |
| A61B 17/29 | (2006.01) | |
| A61B 17/00 | (2006.01) | |
| A61B 17/3201 | (2006.01) | |
| A61B 18/14 | (2006.01) | |
| A61B 90/00 | (2016.01) | |

(52) U.S. Cl.
CPC .............. *A61B 17/29* (2013.01); *A61B 17/00* (2013.01); *A61B 17/3201* (2013.01); *A61B 18/1445* (2013.01); *A61B 2017/00473* (2013.01); *A61B 2017/00477* (2013.01); *A61B 2017/2901* (2013.01); *A61B 2017/292* (2013.01); *A61B 2017/2902* (2013.01); *A61B 2017/2931* (2013.01); *A61B 2018/146* (2013.01); *A61B 2090/0813* (2016.02)

(58) Field of Classification Search
CPC ..... A61B 17/00; A61B 17/29; A61B 17/3201; A61B 18/1445; A61B 2017/00473; A61B 2017/00477; A61B 2017/2901; A61B 2017/2902; A61B 2017/292; A61B 2017/2931; A61B 2018/146; A61B 2019/4868
See application file for complete search history.

(56) References Cited

U.S. PATENT DOCUMENTS

| | | | |
|---|---|---|---|
| 5,282,806 A * | 2/1994 | Haber | A61B 17/29 606/139 |
| 5,618,308 A | 4/1997 | Holmes et al. | |
| 5,817,128 A | 10/1998 | Storz | |
| (Continued) | | | |

FOREIGN PATENT DOCUMENTS

| | | | |
|---|---|---|---|
| DE | 9215053 U1 | 4/1993 | |
| DE | 19722062 A1 | 12/1998 | |
| (Continued) | | | |

*Primary Examiner* — Michael Peffley
*Assistant Examiner* — Amanda Zink
(74) *Attorney, Agent, or Firm* — Whitmyer IP Group LLC

(57) ABSTRACT

A shaft for a rigid endoscopic instrument includes an elongate outer shaft and an elongate transmission element that can be arranged movably inside the outer shaft, wherein the outer shaft includes a proximal portion and a distal portion, which can be connected releasably to each other. The invention also relates to a rigid endoscopic instrument having such a shaft.

18 Claims, 9 Drawing Sheets

(56) References Cited

U.S. PATENT DOCUMENTS

| | | | | |
|---|---|---|---|---|
| 7,913,891 B2* | 3/2011 | Doll | ................ | A61B 17/07207 227/175.2 |
| 2005/0131396 A1* | 6/2005 | Stanczak | ........ | A61B 17/320016 606/1 |
| 2008/0021278 A1* | 1/2008 | Leonard | ............. | A61B 17/1608 600/129 |
| 2011/0319888 A1* | 12/2011 | Mueller | ............. | A61B 18/1445 606/41 |
| 2012/0059408 A1* | 3/2012 | Mueller | ................ | A61B 17/29 606/206 |

FOREIGN PATENT DOCUMENTS

| | | |
|---|---|---|
| DE | 102005021234 A1 | 11/2006 |
| DE | 102006034590 A1 | 2/2007 |
| DE | 102006028001 A1 | 12/2007 |
| DE | 102012007651 A1 | 10/2013 |
| EP | 0688187 B1 | 6/1998 |
| EP | 0925028 B1 | 9/2001 |
| EP | 1400211 A1 | 3/2004 |
| EP | 1721577 A1 | 11/2006 |
| EP | 2399538 A2 | 12/2011 |
| EP | 2653117 A1 | 10/2013 |
| WO | 9801080 A1 | 1/1998 |
| WO | 2008005433 A1 | 1/2008 |

\* cited by examiner

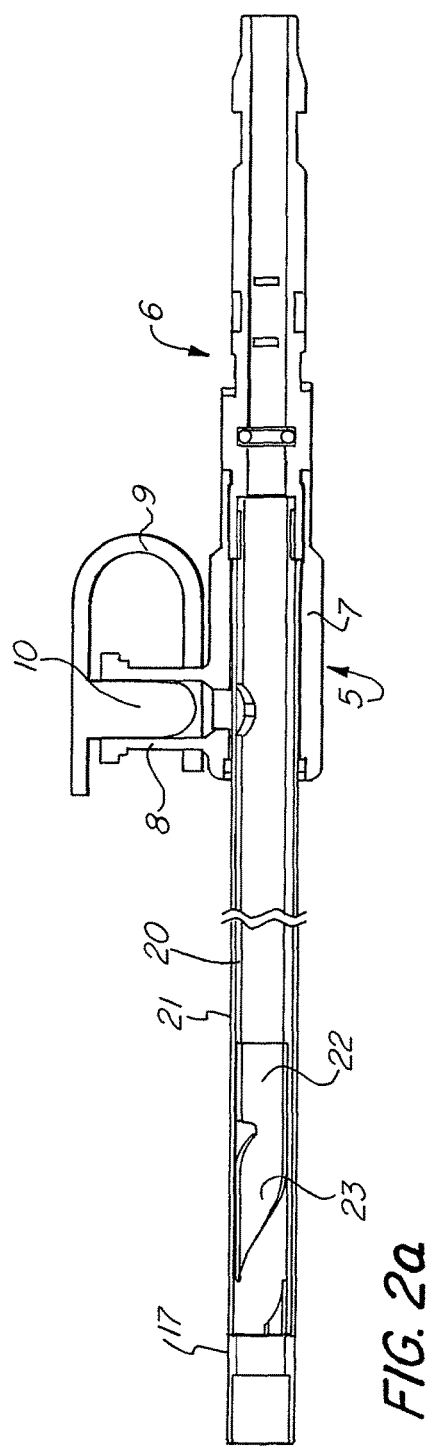
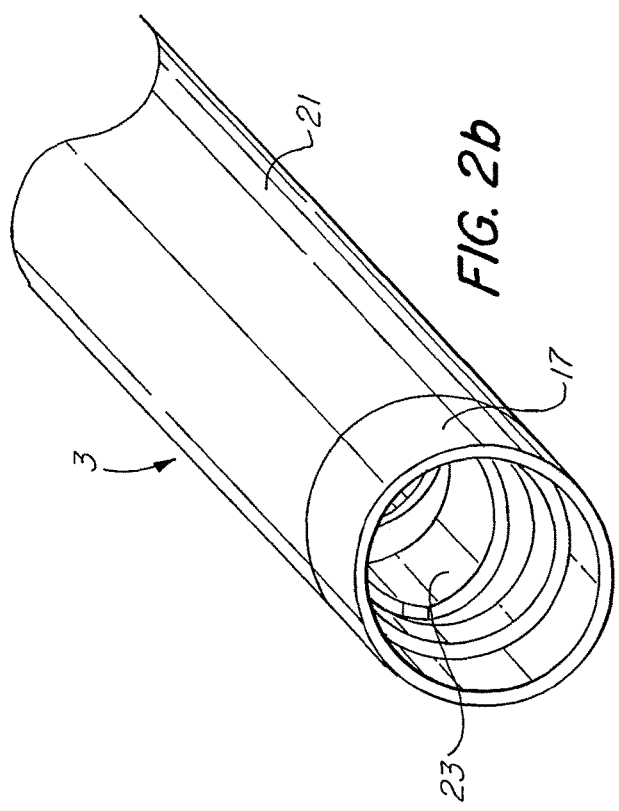
FIG. 2a
FIG. 2b

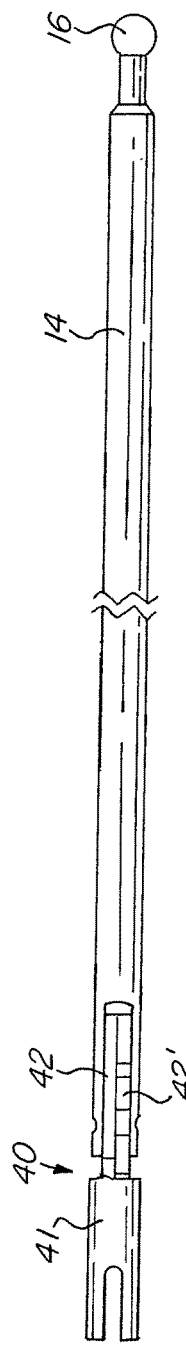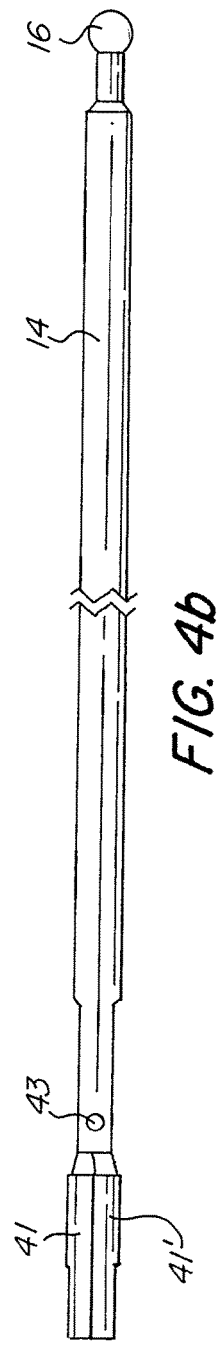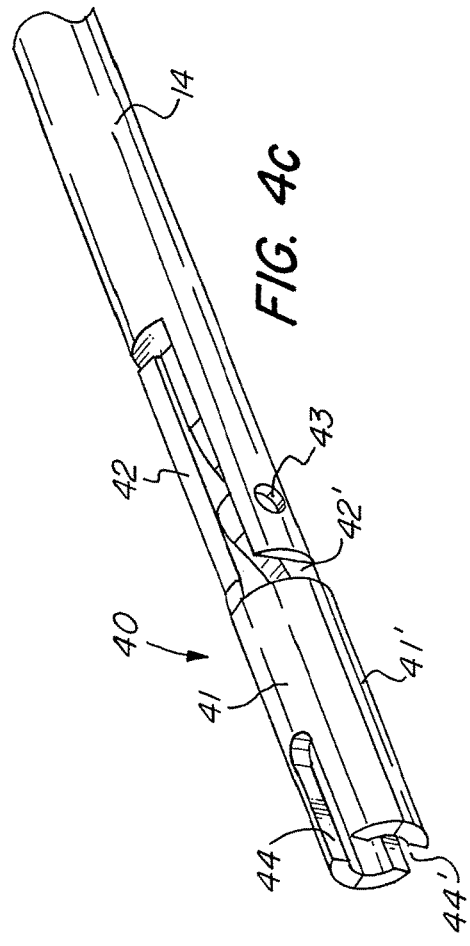

ENDOSCOPIC INSTRUMENT, AND SHAFT FOR AN ENDOSCOPIC INSTRUMENT

FIELD OF THE INVENTION

The present invention relates to a shaft for a rigid endoscopic instrument, comprising an elongate outer and an elongate transmission element that can be arranged movably inside the outer shaft. Endoscopic instrument is used here to designate instruments for micro-invasive surgical procedures whether or not the procedure is accompanied by endoscopy. The invention further relates to a rigid endoscopic instrument with an elongate shaft, a tool arranged at a distal end of the shaft, and a handle arranged at a proximal end of the shaft, wherein the shaft comprises an elongate outer shaft and an elongate transmission element arranged movably inside the outer shaft, and wherein the tool and the handle are connected to the transmission element and to the outer shaft in such a way that the tool can be actuated by the handle by means of a movement of the transmission element relative to the outer shaft.

BACKGROUND OF THE INVENTION

Endoscopic operating techniques have become widely used in a large number of surgical procedures. In these procedures, an endoscopic instrument set, which in particular can comprise an endoscope and one or more endoscopic instruments, is guided through a natural opening of the body, or through an artificial opening created with the aid of an incision, to an operating site located inside the body. For this purpose, endoscopic instruments have an elongate shaft with, at the distal end thereof, i.e. the end remote from the user, a tool for performing surgical manipulations, which tool can be actuated from a handle arranged at the proximal end of the shaft, i.e. the end near the user, and via and elongate transmission element arranged in the shaft. In an endoscopic procedure, the handle remains outside the body opening, while the shaft with the tool is introduced through the body opening. The necessary usable length of the shaft, for guiding the tool to the operating site via the access route created through the natural or artificial opening in the body, depends in particular on the nature of the surgical procedure and on the access route used, in particular on the length of the access route between the natural or artificially created opening in the body and the operating site. Moreover, the nature of the procedure and the access route used for the latter will dictate whether a rigid, a semi-flexible or a flexible endoscopic instrument set is used.

In laparoscopic operations, but also in other endoscopic procedures, it is rigid endoscopic instruments that are mainly used. In these, the elongate shaft is substantially rigid or only slightly flexible. While a useful maximum length of ca. 500 mm is generally sufficient for laparoscopic procedures, it may in some cases be necessary to provide a sometimes substantially greater usable length, for example in the case of obese patients.

Rigid endoscopic instruments are often provided for multiple use. Therefore, after a procedure has been completed, the used endoscopic instrument has to be cleaned and sterilized before being used again. For this purpose, it is known for endoscopic instruments to be designed such that they can be dismantled, in which case in particular the handle can be separated from the shaft. Moreover, a shaft insert, which comprises the tool and the transmission element, can be designed to be removable from an outer shaft of the shaft. The handle, the outer shaft and the insert can then be cleaned in a manner known per se in a surgical washing machine and sterilized in an autoclave. Since the available space in such cleaning and sterilizing apparatuses is limited, instruments with an excess useful length, particularly with a length of more than 500 mm, cannot be cleaned and sterilized in this way, or they can be cleaned and sterilized in this way only with considerable effort, for example with manual cleaning and sterilization in a specially adapted autoclave.

SUMMARY OF THE INVENTION

It is an object of the present invention to make available a shaft for a rigid endoscopic instrument which is suitable for use in a particularly long endoscopic access route and which is easier to clean and sterilize. It is also an object of the present invention to create an endoscopic instrument of this kind.

This object is achieved by a shaft for an endoscopic instrument according to the invention.

Advantageous developments of the invention are set forth in the dependent claims.

A shaft according to the invention is designed as a shaft for a rigid endoscopic instrument, in particular for performing endoscopic surgical procedures. The shaft according to the invention is of elongate design for insertion into a cavity inside the body by way of an endoscopic access route and comprises an elongate, substantially rigid outer shaft and a likewise elongate transmission element, wherein the outer shaft and the transmission element are designed in such a way that the transmission element can be arranged movably inside the outer shaft. Moreover, the outer shaft and the transmission element are designed in such a way that a tool is connected or can be connected to a distal end area of the shaft and a handle is connected or can be connected to a proximal end area of the shaft, such that the tool can be actuated by actuation of the handle. For this purpose, the outer shaft and the transmission element are connected or can be connected at their respective distal ends to the tool and at their respective proximal ends to the handle, such that the transmission element is moved relative to the outer shaft by an actuation of the handle, and the tool is actuated by the movement of the transmission element. The handle can preferably be connected releasably to the proximal end of the shaft. For this purpose, a proximal end area of the outer shaft and of the transmission element can be designed in the manner disclosed in EP 0 688 187 B1 and DE 197 22 062 A1, which are incorporated by reference into the present application. The outer shaft can be insertable directly into an opening in the body or can be designed, for example, to be inserted by means of a trocar.

The transmission element can be rigid or flexible. The transmission element is preferably designed as a pull rod which is movable relative to the outer shaft in a longitudinal direction of the shaft and which can transmit pulling forces and, at least to a limited extent, also pushing forces. In certain designs, the transmission element can also transmit torsional forces. By an actuation of the handle, the transmission element or the pull rod can be moved relative to the outer shaft in the longitudinal direction and, in this way, a movable part of the tool can be moved.

According to the invention, the outer shaft comprises a proximal portion and a distal portion, which can be connected releasably to each other. The distal portion is connected or can be connected to the tool, and the proximal portion is connected or can be connected to the handle. The proximal portion and the distal portion are both substantially rigid. Preferably, the two portions are approximately the same length and are each about half the length of the outer shaft.

By virtue of the fact that the outer shaft is divided into two longitudinal portions that can be connected to each other and can be separated from each other, the instrument is able to be dismantled, as a result of which cleaning and sterilization are made easier. Designing the outer shaft in such a way that it can be dismantled also allows an endoscopic instrument with excess usable length to be cleaned and sterilized in cleaning and sterilizing apparatuses that are designed for instruments with a shorter useful length. For this purpose, provision is preferably made that the portions of the outer shaft that can be connected releasably to each other each have a length which corresponds at most to the length of the shaft of standard instruments, in particular at most 500 mm. Such a proximal portion and distal portion of the outer shaft can therefore be treated in cleaning and sterilizing apparatuses that are designed for standard instruments and can be stored in standard baskets that are dimensioned for standard instruments.

Preferably, the proximal portion of the outer shaft has a connection element at its distal end, and the distal portion of the outer shaft has a connection element at its proximal end, said connection elements being provided for releasable connection to each other, as a result of which the interconnected portions of the outer shaft form a rigid outer shaft of correspondingly greater length. The connection elements can be fixedly connected to the respective portion of the outer shaft or can be made in one piece therewith. The connection elements can each be designed as an axially directed projection or can have such a projection, wherein the projections of the proximal portion and of the distal portion of the outer shaft are designed complementing each other in such a way that they are able to engage in each other. In particular, the projections each have an undercut in the axial direction, wherein the undercuts of the projections are designed complementing each other in order to permit mutual engagement. In this way, a secure force-fit or form-fit connection can be achieved.

In a particularly advantageous manner, the connection element assigned to the proximal portion of the outer shaft and the connection element assigned to the distal portion of the outer shaft have respective complementary helices engaging in each other. Each connection element can also have a plurality of helices, which interact with complementary helices of the other connection element. The connection elements can have at least one projection each, which are designed as mutually complementary helices, or, at least in one of the connection elements, it is possible to form on the inside face or outside face of an axially directed tube a helix with which a complementary helix of the other connection element cooperates. In particular, the distal edge of the projection of the distal portion of the outer shaft forms a helical line, and the proximal edge of the projection of the proximal portion likewise forms a helical line, wherein both helical lines preferably have the same pitch. The edge of the projection lying opposite the edge forming the helical line can also represent a helical line. By virtue of the fact that the connection elements of the distal portion and proximal portion of the outer shaft have respective complementary mutually engaging helices, the outer shaft can be assembled and dismantled in a simple and reliable manner. Moreover, this permits a design of the connection elements that does not lead to an increase in the external diameter of the outer shaft and that does not result in a substantial narrowing of the usable internal space inside the outer shaft.

Preferably, the helix of the proximal portion of the outer shaft is arranged substantially between the distally extended inner and outer envelope surfaces of the proximal portion of the outer shaft, and the helix of the distal portion of the outer shaft is arranged between the proximally extended inner and outer envelope surfaces of the distal portion of the outer shaft. By virtue of the fact that, in the area of the connection elements, the external diameter of the outer shaft is not increased and the internal diameter is not substantially reduced, it is easy to insert the shaft through the endoscopic access route, and it is possible to avoid limiting the mobility of the transmission element inside the outer shaft.

Although they are described as being preferably constant, the two helices may also not be constant, in other words can have pitches that decrease or increase in the axial direction. Particularly increasing, that is to say changing from a more axial orientation to a more tangential orientation in the direction from the cylindrical main shaft to the ends of the helix. To achieve this "geometrically", that is to say without gaps in the assembled shaft, the helices here have to narrow in the axial direction starting from the cylindrical main shaft, and the helix seats accordingly have to increase in size. Of course, in the axial direction starting from the cylindrical main shaft, the helices can also narrow without their pitch changing, i.e. also with a constant pitch.

According to a preferred embodiment of the invention, the transmission element comprises a proximal portion and a distal portion, which can be connected releasably to each other in order to transmit forces acting in the longitudinal direction. The proximal portion of the transmission element is also designed for releasable connection to the handle, and the distal portion of the transmission element is connected or can be connected to the tool; the distal portion of the transmission element can be connected movably but inseparably via the tool to the distal portion of the outer shaft. In terms of their respective lengths, the proximal portion and the distal portion of the transmission element can have approximately the length of the proximal portion and distal portion, respectively, of the outer shaft. In particular, the proximal portion and the distal portion each have about half the length of the transmission element. Preferably, the length of the distal portion of the transmission element is such that, when the tool is connected to the distal portion of the transmission element and to the distal portion of the outer shaft, the distal portion of the transmission element protrudes from the proximal end of the distal portion of the outer shaft. Correspondingly, the length of the proximal portion of the transmission element can be such that the proximal end of the transmission element protrudes from the proximal end of the outer shaft in the proximal direction when the proximal portion and the distal portion of the outer shaft and of the transmission element are connected to each other. By virtue of the fact that the transmission element has a proximal portion and a distal portion that can be connected to each other and can be separated from each other, the shaft is made even easier to clean and/or sterilize, especially if the transmission element is of rigid design.

It is also preferable that the proximal portion and the distal portion of the transmission element each have a connection element to permit a releasable, form-fit connection of the distal and proximal portion to each other. The connection elements of the proximal portion and distal portion of the transmission element can, for example, be designed in one piece with the respective portion or can be fixedly connected thereto. By virtue of the fact that a form-fit connection between the distal portion and the proximal portion of the transmission element can be created, a secure connection for the transmission of high forces for actuating the tool is permitted in a simple manner.

According to a particularly preferred embodiment of the invention the connection element assigned to the proximal portion of the transmission element and the connection element assigned to the distal portion of the transmission element can be connected to each other in such a way that, when the connection elements are arranged inside the outer shaft, or a portion of the outer shaft, the proximal portion and the distal portion are connected non-releasably to each other and, consequently, the proximal portion and the distal portion of the transmission element are also connected non-releasably to each other. If the connection elements of the transmission element are not enclosed by the outer shaft, the connection elements can be separable from each other without application of force or can be connected to each other merely by a force fit. For this purpose, for example, a form-fit element can be provided which, by means of a transverse movement, effects a form-fit connection between the connection elements of the two portions of the transmission element and which is blocked by the outer shaft from freeing the form-fit connection, in particular by a transverse movement of the form-fit element being prevented by the outer shaft. The form-fit element can be part of one of the connection elements of the portions of the transmission element or can be used in addition to these. This permits simple assembly and dismantling of the shaft, with particularly safe transmission of the forces needed to actuate the tool. Moreover, inadvertent separation of the proximal portion and distal portion of the transmission element can in this way be safely prevented in the assembled state.

Advantageously, the connection elements of the proximal portion and of the distal portion of the transmission element are designed for producing a snap-fit connection with at least one jaw or barb, preferably two jaws or barbs, mounted in an articulated or elastically resilient manner. The jaws or barbs mounted in an articulated or elastically resilient manner can be assigned to the proximal portion or distal portion of the transmission element, wherein the respective other portion has an undercut cooperating with the jaws or barbs. The connection can in particular be a form-fit connection. An outer contour of the jaws or barbs can be configured such that a release of the connection is safely prevented by the attached outer shaft, since a deflection of the jaws or barbs that is needed to open the connection is blocked by the outer shaft. A snap-fit connection of this kind is connectable in a particularly reliable and particularly simple way.

According to another preferred embodiment of the invention, the connection elements can be pushed into each other in a direction transverse to the longitudinal axis of the shaft, wherein securing can additionally be provided by a securing pin that can be inserted into the transmission element transversely with respect to the longitudinal direction thereof. In particular, the connection can be a form-fit connection. Preferably, when the transmission element is arranged in the outer shaft, the connection elements are connected to each other non-releasably, wherein a lateral pulling apart or a removal of the securing pin in order to release the connection is blocked with a form fit by the outer shaft. In this way too, a connection is obtained that is particularly secure and easy to produce and release.

According to another preferred embodiment of the invention, a connection is provided that is mutually connectable and separable by rotation of the distal portion relative to the proximal portion of the transmission element, which connection is designed as a bayonet connection or threaded connection, for example. Preferably, the thread direction is oriented counter to the direction of a helix which is formed by interacting connection elements of the proximal portion and of the distal portion of the outer shaft. In this way, a connection of the portions of the transmission element is likewise obtained that is secure and easy to connect and release.

According to a particularly preferred embodiment of the invention, the distal portion and the proximal portion of the transmission element can be connected to each other in a manner secure against twisting, the distal portion of the transmission element is connected or can be connected to the distal portion of the outer shaft in a manner secure against twisting, and the proximal portion of the transmission element can be connected to the proximal portion of the outer shaft in a manner secure against twisting. A connection secure against twisting between the proximal portion and distal portion of the transmission element can be achieved in particular by a suitable design of the connection elements assigned to the proximal portion and to the distal portion, for example by a design of the connection elements that is not axially symmetrical and/or by a pin inserted in the transverse direction. In this way, an axial twisting of the two portions relative to each other can be prevented. Moreover, the distal portion of the transmission element is connected or can be connected to the distal portion of the outer shaft in a manner secure against twisting, for example by a pin guided in a groove or in a slot and oriented transversely with respect to the longitudinal axis of the shaft. Moreover, the proximal portion of the outer shaft is connected to the proximal portion of the transmission element in a manner secure against twisting. This can be achieved, for example, by the proximal portion of the transmission element and the proximal portion of the outer shaft having a non-axially-symmetrical design in their respective proximal end area. Particularly advantageously, the proximal portion and the distal portion of the transmission element, likewise the proximal portion and the distal portion of the outer shaft, are themselves each designed to be as rotationally stiff as possible. In this way, the proximal portion is secured against twisting relative to the distal portion of the outer shaft, as a result of which an inadvertent release of a connection releasable by relative rotation can be safely prevented between the proximal portion and the distal portion of the outer shaft.

Particularly preferably, when a handle is connected to the shaft, the proximal portion of the outer shaft is connected to the proximal portion of the transmission element in a manner secure against twisting. Such a connection is preferably designed as described in EP 0 688 187 B1. It is thereby possible to achieve the additional particular advantage that dismantling of a shaft, in which the outer shaft is created by the proximal portion being connected to the distal portion in a way that is releasable by relative rotation, is possible only after separation of the handle from the shaft, and therefore inadvertent dismantling during an operation can be reliably prevented. However, after the operation, the instrument is easy to dismantle.

According to a preferred embodiment of the invention, the shaft is designed as a shaft for an electrosurgical endoscopic instrument, wherein current is transmitted to the tool via the transmission element, which for this purpose is metallic and is electrically conductively connected to the tool and to an HF attachment or can be brought into such connection. In particular, the tool is electrically conductively connected to the distal portion of the transmission element, and the proximal portion of the transmission element can be electrically conductively connected to an HF attachment arranged on the handle. The tool is preferably also made of a metallic material. Preferably, the outer shaft is enclosed by an insulation, which can be designed for example as a shrink-on hose. A tubular insulating piece can be arranged at the distal end of the proximal portion of the outer shaft and/or at the proximal end of the distal portion of the outer shaft, as a result of which it is possible to prevent the development of a creepage distance in the assembled state.

A rigid endoscopic instrument according to the invention comprises a substantially rigid, elongate shaft, a tool arranged at a distal end of the shaft, and a handle arranged at a proximal end of the shaft. The shaft comprises an elongate outer shaft and an elongate transmission element arranged movably inside the outer shaft. The tool and the handle are connected to the transmission element and the outer shaft in such a way that the tool can be actuated by the handle by means of a movement of the transmission element relative to the outer shaft. According to the invention, the shaft is designed as has been described above. The endoscopic instrument has in particular an excess length and is suitable for use in particularly long endoscopic access routes. In particular, the fact that the outer shaft can be dismantled into a proximal portion and a distal portion means that cleaning and sterilization can be performed in appliances with standard dimensions.

The tool is designed in particular for performing surgical manipulations in a cavity that is located inside the body and that can be reached via the access route, and for this purpose it can have two tool elements interacting with each other. For example, the tool can be in the form of surgical scissors or gripping forceps with one or two movable scissor parts or jaw parts that are pivotable relative to each other, wherein one movable tool element is connected in an articulated manner to a stationary tool element, or it is possible for two movable tool elements to be connected to each other via a hinge. The stationary tool element or the hinge is connected to a distal end area of the outer shaft, and the one or more movable tool elements are connected to the transmission element via a lever arrangement or vice versa. In this way, by means of a longitudinal movement of the transmission element, it is possible in a manner known per se to obtain a pivoting movement of the scissors or jaw parts relative to each other, for example as is disclosed in the patent specification DE 10 2006 028 001 B4, which in this context is incorporated by reference into the present application. However, the tool can also comprise, for example, an axially movable tool element, which is connected directly to the transmission element. The tool can be releasable from the shaft, or it can be connected inseparably, but in an articulated manner, to the distal portion of the outer shaft and/or to the transmission element or the distal portion of the transmission element.

The handle is preferably separable from the proximal end of the shaft and can be connected thereto again. For this purpose, a proximal end area of the outer shaft and of the transmission element can be designed in the manner described in EP 0 925 028 B1 and DE 197 22 062 A1. The handle can be designed to be fitted, in the manner known from these documents, onto the proximal end of the proximal portion of the outer shaft.

To assemble an endoscopic instrument with a shaft of the kind described above, the following steps in particular are taken:

In a first step, the connection element of the distal portion of the transmission element is connected to the connection element of the proximal portion of the transmission element. This results in the transmission element serving to transmit forces in the longitudinal direction for actuation of the tool of the endoscopic instrument. If the distal portion of the outer shaft is movable over the tool with the distal portion of the pull rod but connected inseparably thereto, the transmission element is connected to the tool and to the distal portion of the outer shaft. In the second step, the proximal portion of the outer shaft is pushed, from the proximal direction, over the part of the transmission element protruding in the proximal direction from the distal portion of the outer shaft. With the aid of the connection elements of the proximal portion and distal portion of the outer shaft, the two portions of the outer shaft are connected to each other and now form the continuous, rigid outer shaft of the endoscopic instrument, in which the transmission element is arranged. The assembly of the shaft is then complete.

In a further step, the handle is connected to the shaft, for example by means of a proximal end area of the outer shaft with a connection mechanism arranged thereon being pushed into a coupling of the handle. The handle comprises a stationary part and a movable part, wherein the tool can be actuated by moving the movable part relative to the stationary part. Moreover, the handle can comprise a rotary wheel for rotating the outer shaft and correspondingly changing the orientation of the tool, and also a lock mechanism for additionally locking the outer shaft in the handle, and an electrical attachment for an HF cable.

To dismantle the endoscopic instrument, the outer shaft is removed from the coupling of the handle, for which purpose, for example, the movable part of the handle is bought to a dismantling position and a push-button of the lock mechanism is pressed. The proximal portion of the outer shaft is separated from the distal portion by separation of the connection elements of the outer shaft and pulled off in the proximal direction over the transmission element. By separation of the connection elements of the transmission element, the distal portion and the proximal portion of the transmission element are released from each other. The individual elements of the endoscopic instrument each have a smaller length than the overall length of the assembled instrument, for example only half the length, and can be stored in a standard basket and cleaned and sterilized in standard cleaning and sterilizing apparatuses.

It will be appreciated that the features mentioned above and those still to be explained below can be used not only in the respectively cited combination but also in other combinations or singly, without departing from the scope of the present invention.

BRIEF DESCRIPTION OF THE DRAWINGS

Further aspects of the invention will become clear from the following description of a preferred illustrative embodiment and from the attached drawing, in which:

FIGS. 2a and 2b show the proximal portion of the outer shaft according to FIG. 1 in a longitudinal section and in a perspective view, respectively;

FIGS. 4a to 4c show the proximal portion of the transmission element in two side views and a perspective view;

FIG. 10b shows a perspective view of one of the connection elements according to FIG. 10a;

DETAILED DESCRIPTION OF THE INVENTION

Figure 1:
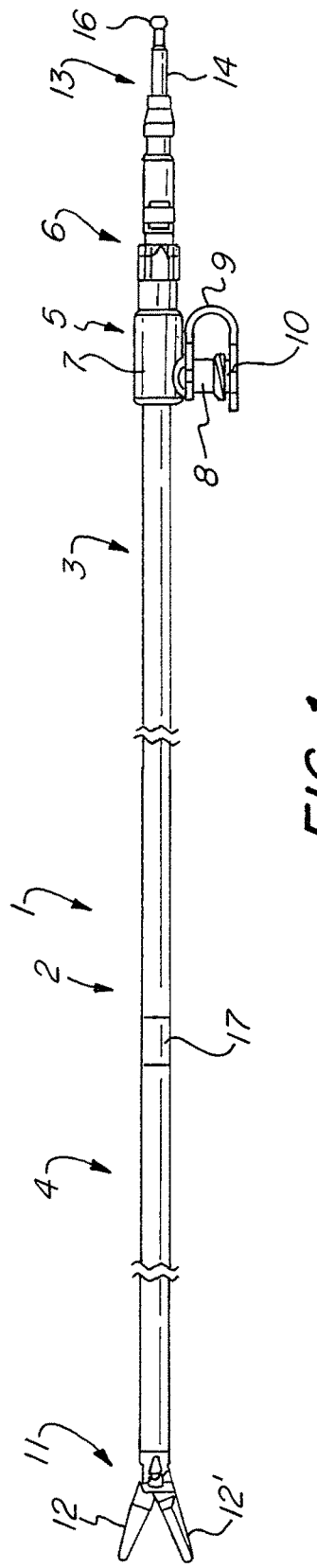
FIG. 1 shows a side view of a shaft according to the invention with a tool arranged at its distal end.

As is shown by way of example in FIG. 1, a shaft 1 for an endoscopic instrument comprises an elongate outer shaft 2, which is divided into a proximal portion 3 and a distal portion 4. The proximal portion 3 of the outer shaft 2 has an irrigation attachment 5 and a connection mechanism 6 for connecting to a handle. The irrigation attachment 5 comprises a sleeve 7, which is adjoined by an attachment nozzle 8 that is provided for attaching an irrigation hose or suction hose with the aid of a Luer lock and that can be closed by a stopper 10 held securely in place by a tab 9. The connection mechanism is designed in such a way that a handle 50 can be attached rotatably, and the outer shaft 2 can be rotated relative to the handle about the longitudinal axis of the outer shaft 2 via a rotary wheel 52 that can be connected to the proximal end area of the proximal portion 3 of the outer shaft 2 for conjoint rotation therewith (see FIG. 6). A tool 11 is connected to the distal portion 4 of the outer shaft 2 and, in the illustrative embodiment shown, is designed as scissors with two scissor blades 12, 12' that are pivotable relative to the distal portion 4 of the outer shaft 2.

Inside the outer shaft 2, a pull rod 13 is arranged movably in the longitudinal direction of the outer shaft 2. As is described in more detail below, the pull rod 13 comprises a proximal portion 14 and a distal portion 15 (not visible in FIG. 1), wherein the proximal portion 14 of the pull rod 13 is arranged substantially inside the proximal portion 3 of the outer shaft 2, and the distal portion 15 of the pull rod 13 is arranged substantially inside the distal portion 4 of the outer shaft 2. The proximal end of the proximal portion 14 of the pull rod 13 is formed by a connection element, for example a ball 16, which can be connected to a movable part of the handle in order to move the pull rod 13 in the longitudinal direction by actuation of the movable part. The pull rod 13 is designed in such a way that it can transmit both pulling forces and also pushing forces in the longitudinal direction of the shaft 1. The distal end area of the distal portion 15 (not visible in FIG. 1) of the pull rod 13 is connected to the movable scissor blades 12, 12' via a lever mechanism, in such a way that the scissor blades 12, 12' can be opened by moving the pull rod 13 in the distal direction and can be closed by moving the pull rod 13 in the proximal direction. The distal end area of the proximal portion 3 of the outer shaft 2 is formed by an insulating sleeve 17. The shaft 1 has an excess length and permits a usable length of more than 500 mm, for example.

As is shown in a longitudinal section in FIG. 2a, the outer shaft comprises a metallic tube 20 enclosed by an insulation, which is formed for instance by a shrink-on hose 21 shrunk onto the tube 20. In the distal end area of the tube 20, a tubular insert 22 is inserted into said tube 20 and connected firmly thereto, which tubular insert 22 is designed in the distal area in the form of a first helix 23. In the area of the insert 22, the continuous hollow space of the proximal portion 3 of the outer shaft 2 is narrowed only very slightly. The distal end of the proximal portion 3 of the outer shaft 2 is formed by the insulating sleeve 17, which is firmly connected to the insert 22 and to the tube 20 and is made of a plastics material. In the proximal end area, the proximal portion 3 of the outer shaft 2 has an irrigation attachment 5 for attaching an irrigation or suction device, and a connection mechanism 6 for connecting to a handle.

In FIG. 2b, the distal end area of the proximal portion of the outer shaft 2 is shown in a perspective view seen obliquely from the distal direction. The insulating sleeve 17 adjoining the shrink-on hose 21 at the distal end can be seen here, inside which insulating sleeve 17 part of the first helix 23 is visible. For reasons of clarity of the drawings, round contours are depicted here as polygon lines.

Figure 3A:
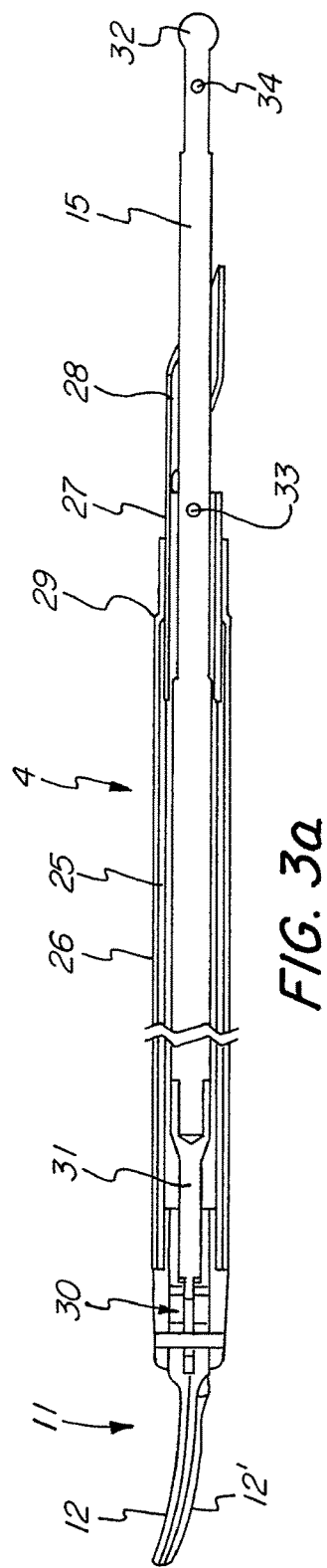
FIGS. 3a and 3b show the distal portion of the outer shaft with the tool and with the distal portion of the transmission element in a longitudinal section and a side view, respectively.
Figure 3B:
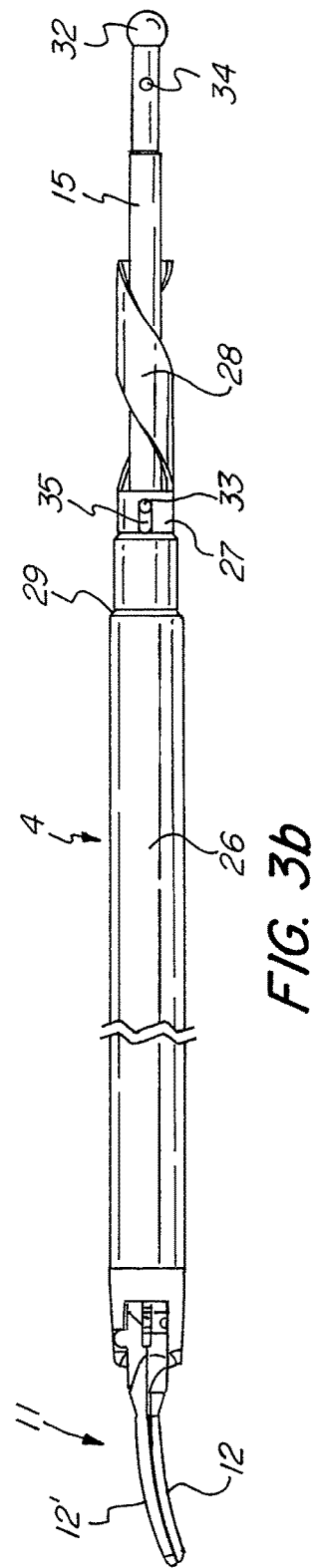

FIGS. 3a and 3b show the distal portion 4 of the outer shaft 2 with the tool 11 and with the distal portion 15 of the pull rod 13 arranged longitudinally movably in the distal portion 4 of the outer shaft 2. The distal portion 4 of the outer shaft 2 comprises an in particular metallic tube 25 enclosed by an insulation, for example a shrink-on hose 26. The shrink-on hose 26 forms a shoulder 29 over the proximal edge of the tube 25. In the proximal end area of the tube 25, a tubular insert 27 is inserted into said tube 25 and connected firmly thereto, which tubular insert 27 runs out in the proximal area into a second helix 28. In the area of the insert 27, the interior of the distal portion 4 of the outer shaft is narrowed only slightly. The insert 27 with the second helix 28 has an external diameter corresponding approximately to the internal diameter of the tube 20 of the proximal portion 3 of the outer shaft in the distal end area thereof and to the internal diameter in a portion of the insulating sleeve 17. The second helix 28 is designed complementing the first helix 23 in such a way that they can be brought into engagement with each other by a helical movement of the distal portion 4 relative to the proximal portion 3 of the outer shaft 2 by a rotation through ca. 360°.

Although measuring ca. 360° in the above illustrative embodiment, the connection of the two helices can also take place through smaller or also greater angles. In addition, the pitch of the helices does not have to be constant as seen in the axial direction, and instead it could change, in particular change continuously, in particular decrease, that is to say could change from a more axial orientation to a more tangential orientation in the direction from the cylindrical main shaft to the ends of the helix. To achieve this "geometrically", that is to say without gaps in the assembled shaft, the helices here have to narrow in the axial direction starting from the cylindrical main shaft, and the helix seats accordingly have to increase in size. Of course, in the axial direction starting from the cylindrical main shaft, the helices can also narrow without their pitch changing, i.e. with a constant pitch.

The internal and external diameter of the insert 27 of the distal portion 4 of the outer shaft 2 with the second helix 28 corresponds substantially to the internal and external diameter of the insert 22 of the proximal portion 3 of the outer shaft 2 with the first helix 23.

As can be seen in FIGS. 3a and 3b, the scissor blades 12, 12' of the tool 11 are connected to the distal end area 31 of the distal portion 15 of the pull rod 13 via a lever mechanism 30. At its proximal end, the distal portion 15 of the pull rod 13 carries a connection element for connecting to the proximal portion 14 of the pull rod 13, wherein the connection element is designed as a ball 32. Moreover, the distal portion 15 of the pull rod 13 has, in its proximal end area, a first pin 33 and a second pin 34, which are each oriented transversely with respect to the longitudinal axis of the pull rod 13, and wherein the first pin 33 protrudes into the axially extending slit 35 of the insert 27 and is guided therein in the longitudinal direction. The length of the slit 35 permits a longitudinal movement of the pull rod 13 sufficient to actuate the tool 11.

As is indicated in FIG. 3a, the hollow space formed by the distal portion 4 of the outer shaft 2 and extending axially to the vicinity of the distal end of the outer shaft 2 is designed in such a way that the distal portion 15 of the transmission element 13 is guided therein with play, as a result of which a space remains between the outside face of the transmission element 13 and the inside face of the outer shaft 2. This space can be used for the passage of an irrigation liquid or a cleaning liquid. In the proximal portion 3 of the outer shaft 2, a space is present which is connected to the space of the distal portion 4 and to the attachment nozzle 8.

In FIGS. 4a to 4c, the proximal portion 14 of the pull rod 13 is shown in two side views (FIGS. 4a and 4b) rotated through 90° relative to each other and in a perspective view (FIG. 4c) seen obliquely from the distal direction. At its proximal end, the proximal portion 14 of the pull rod 13 has a connection element designed as a ball 16 for connecting to a movable part of the handle. At its distal end, the proximal portion 14 of the pull rod 13 has a connection element for connecting to the connection element of the distal portion 15 of the pull rod 13, which element, as shown in FIGS. 4a to 4c, is designed as a snap-fit mechanism 40 for receiving the ball 32 of the distal portion 15 of the pull rod 13. The snap-fit mechanism 40 comprises two interacting jaws 41, 41' which, in the closed position, enclose a substantially cylindrical interior in the form of an axially oriented blind hole, of which the proximal end area has a widening in order to receive the ball 32 (not visible in FIGS. 4a to 4c). The jaws 41, 41' are each mounted pivotably, via a tab 42, 42', on a pin (not shown in FIGS. 4a to 4c) that is guided through the bore 43. At least the tab 42 is elastically bendable and is supported elastically resiliently against the other tab 42' or against the proximal portion 14 of the pulling rod, such that the two jaws 41, 41' can be opened counter to an elastic restoring force and can be closed again by the latter. At their distal end, the jaws 41, 41' each have an axially extending slit 44, 44' open in the distal direction.

Figure 5:
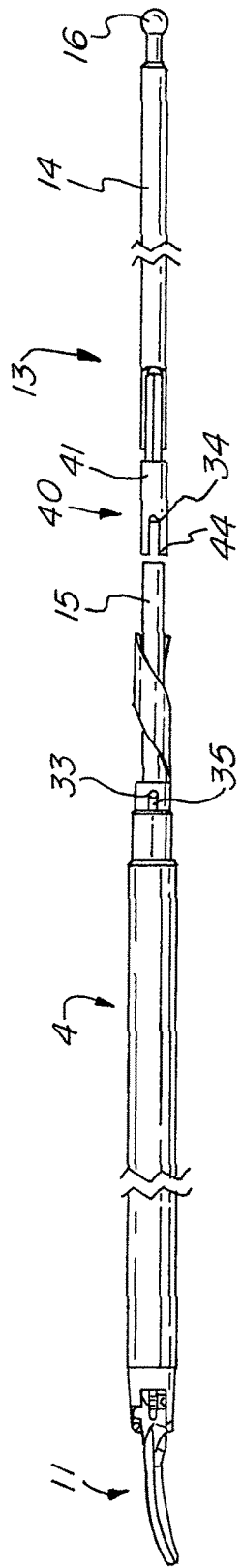
FIG. 5 shows a side view of the distal portion of the outer shaft with the tool and with the transmission element composed of its distal portion and proximal portion.

FIG. 5 shows the distal portion 4 of the outer shaft 2 with the tool 11 and the pull rod 13 which is formed by the proximal portion 14 and the distal portion 15 of the pull rod connected to each other via the snap-fit mechanism 40. The ball 32, which forms the connection element arranged at the proximal end of the distal portion 15 of the pull rod 13, is introduced into the jaws 41, 41' of the snap-fit mechanism 40 and is held by these. As can be seen in FIG. 5, the second pin 34 of the distal portion 15 protrudes into the slit 44 of the jaw 41 and is guided movably therein in the axial direction. It will also be seen from FIG. 5 that the first pin 33 is similarly guided in the longitudinal slit 35 of the insert 27 of the distal portion 4 of the outer shaft 2.

An endoscopic instrument that has the above-described shaft is assembled as follows:

The distal portion 4 of the outer shaft 2 is connected to the distal portion 15 of the pull rod via the tool 11 and the lever mechanism 30 (see FIGS. 3a and 3b). In a first step of the assembly, the connection element of the distal portion 15 of the pull rod 13, namely the ball 32, is connected to the proximal portion 14 of the pull rod 13, by the ball 32 being introduced between the jaws 41, 41' of the snap-fit mechanism 40. In doing so, the second pin 34 is also introduced into the slits 44, 44'. The distal portion 15 is now connected to the proximal portion 14 of the pull rod with a force fit and in a manner secure against twisting (see FIG. 5). In the second step, the proximal portion 3 of the outer shaft 2 is pushed, from the proximal direction, over the proximal portion 14 of the pull rod 13 with the snap-fit mechanism 40 and over the proximal end area of the distal portion 15 of the pull rod 13 and, by means of a helical movement, the first helix 23 of the proximal portion 3 is brought into engagement with the second helix 28 of the distal portion 4 of the outer shaft 2. In this way, the insulating sleeve 17 engages over a proximal end area of the shrink-on hose 26 of the distal portion 4 and lies approximately on the shoulder 29. The assembly of the shaft 1 according to FIG. 1 is now complete.

Figure 6:
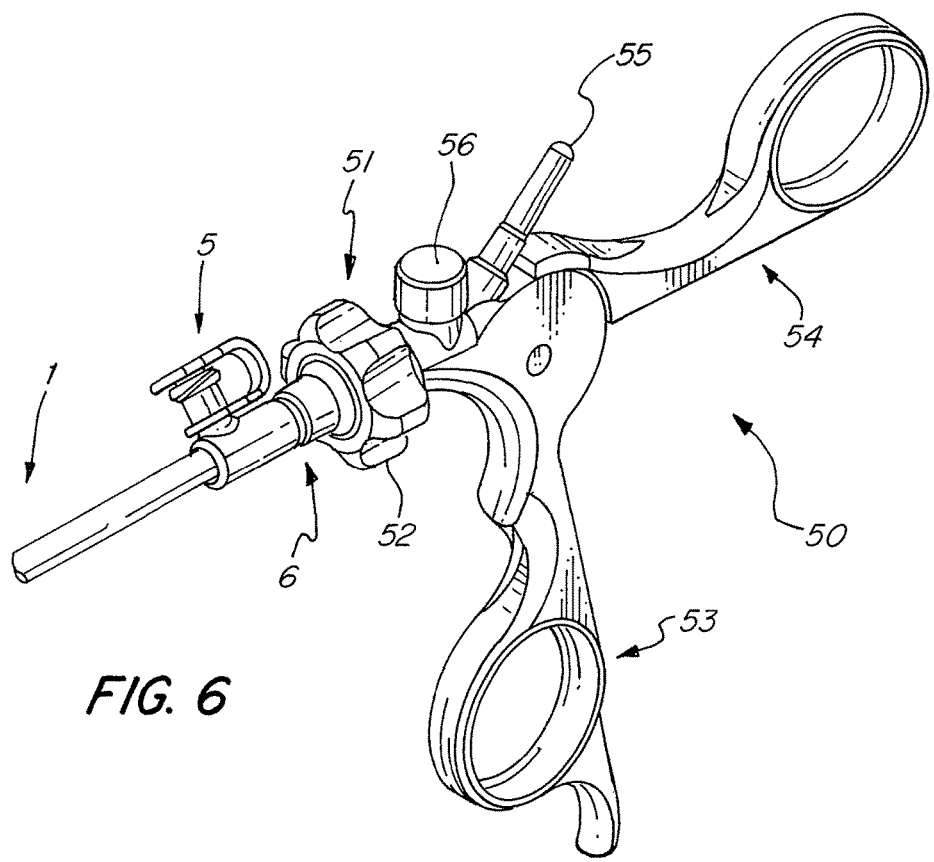
FIG. 6 shows a perspective view of the proximal end area of the shaft with a handle connected thereto.

In a further step, the handle 50 is connected to the shaft 1, by means of the latter being pushed with the connection mechanism 6 into a coupling 51 of the handle 50, as is indicated by the arrow in FIG. 6. In this way, the shaft 1 is held on the handle in such a way that the shaft 1 can be rotated about its longitudinal axis relative to the handle 50 via a rotary wheel 52, and the ball 16, which forms the proximal connection element of the pull rod 13, is in engagement with the pivotable part 53 of the handle 50. The pull rod 13 is moved in the axial direction by actuation of the pivotable part 53. The connection mechanism 6 and the coupling 51 can also be designed for example as disclosed in EP 0 688 187 B1 and DE 197 22 062 A1, in such a way that, via clamping elements enclosed by the handle, a release of the pull rod 13 from the handle 50 is additionally prevented and twisting is avoided, and locking of the shaft 1 in the handle 50 is obtained. As is shown in FIG. 6, the handle 50 also comprises a stationary part 54, an electrical attachment 55 for attaching an HF cable, and a push-button 56 for unlocking the shaft 1. The HF voltage supplied to the instrument via the electrical attachment 55 is transmitted to the tool 11 via the metallic proximal portion 14 and the distal portion 15 of the pull rod 13 and, if appropriate, via the tube 20 and the first and second helices 23, 28 and also the tube 25. The endoscopic instrument shown is a monopolar electrosurgical instrument.

To dismantle the instrument, the pivotable part 53 of the handle 50 is brought to a distal end position for releasing the ball 16, the push-button 56 is actuated, and the shaft 1 is drawn out of the handle 50 in the distal direction. The proximal portion 3 of the outer shaft 2 is then released from the distal portion 4 of the outer shaft 2 by an initially helical movement and then a substantially axial movement, and the proximal portion 14 of the pull rod 13 is withdrawn from the proximal portion 3 of the outer shaft 2. By applying an axial force, the ball 32 is then withdrawn from the jaws 41, 41'. The individual parts, namely the handle 50, the proximal portion 3 of the outer shaft 2 and the distal portion 4 of the outer shaft 2 with the tool 11 and the distal portion 15 of the pull rod 13, each have a much smaller length than the overall length of the assembled endoscopic instrument and can be stored in a basket of standard dimensions and can be cleaned and sterilized in a standard cleaning and sterilizing apparatus. The distal portion 4 of the outer shaft 2, with the tool 11 connected thereto and with the distal portion 15 of the pull rod 13, can usually be cleaned by attachment to an adapter of a cleaning device for irrigating the distal portion 4 of the outer shaft 2, wherein the space present between the distal portion 4 of the pull rod 13 and the distal portion 4 of the outer shaft 2 is used for the passage of the cleaning liquid.

FIGS. 7 to 13 show different designs of the connection between the connection element of the distal portion 15 of the pull rod 13 and the connection element of the proximal portion 14 of the pull rod 13. As is described below, the connection elements can be allocated to the distal portion 15 and the proximal portion 14 respectively, although a reverse allocation is also possible.

Figure 7:
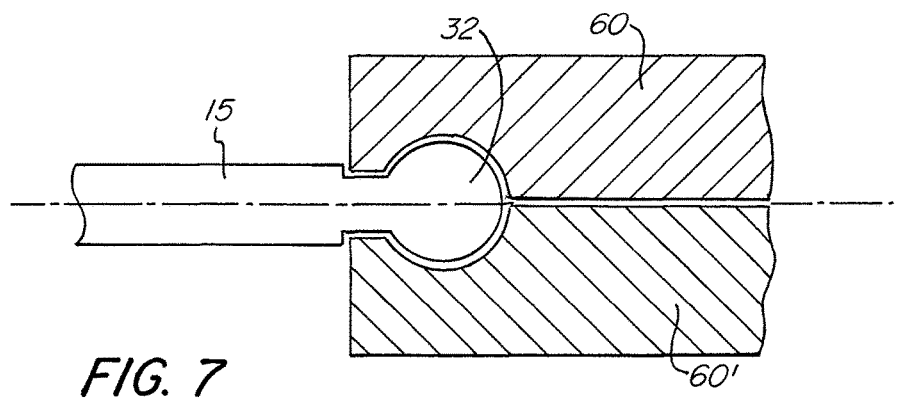
FIGS. 7 to 9 each show in schematic longitudinal section three illustrative embodiments of the connection elements of the proximal portion and distal portion of the transmission element when connected to each other.

According to FIG. 7, the distal portion 15 of the pull rod 13 has, at its proximal end, a ball 32 which is designed as shown in FIGS. 3*a* and 3*b*. The snap-fit mechanism is formed by two half-shells 60, 60' which, in a similar way to that shown in FIGS. 4*a* to 4*c*, are mounted so as to act elastically against each other and hold the ball 32 with a force fit. If the proximal portion 14 of the pull rod 13 is enclosed by the proximal portion 3 of the outer shaft 2, opening of the two half-shells 60, 60' is prevented with a form fit and the ball 32 is thus held with a form fit.

Figure 8:
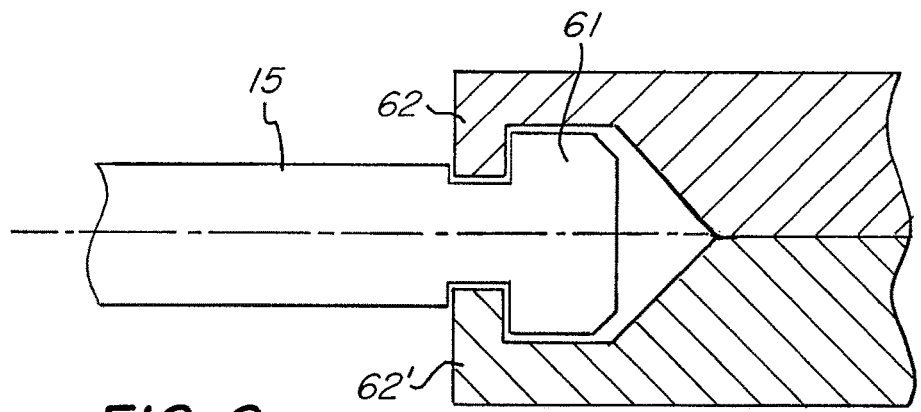

As is shown in FIG. 8, the connection element of the distal portion 15 of the pull rod 13 can also have another form, for example designed as a plate 61 which is gripped with a form fit or force fit by the jaws designed as hooks 62, 62' and is held with a form fit when the instrument is assembled.

Figure 9:
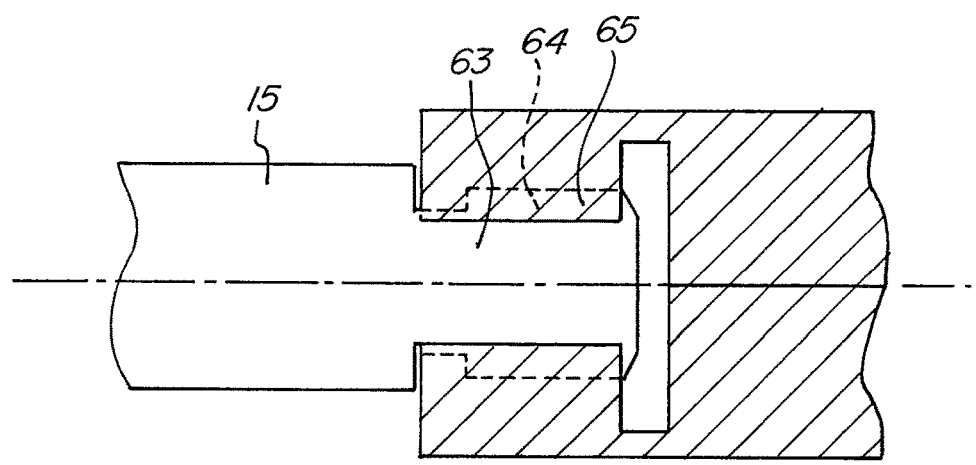

According to FIG. 9, a proximal end portion 63 of the distal portion 15 of the pull rod 13 can have an outer thread 64, which interacts with a corresponding inner thread 65 of the distal end portion of the proximal portion 14 of the pull rod 13. The outer thread 64 and the inner thread 65 have another direction and another pitch than the first and second helices 23, 28 of the proximal portion 3 and distal portion 4, respectively, of the outer shaft 4 (see FIGS. 2*a*, 2*b*, 3*a*, 3*b*). Instead of a thread, a bayonet-like connection can likewise be provided, wherein the direction for opening and closing the bayonet is likewise directed counter to the direction of rotation for opening and closing the connection of the helices 23, 28.

Figure 10A:
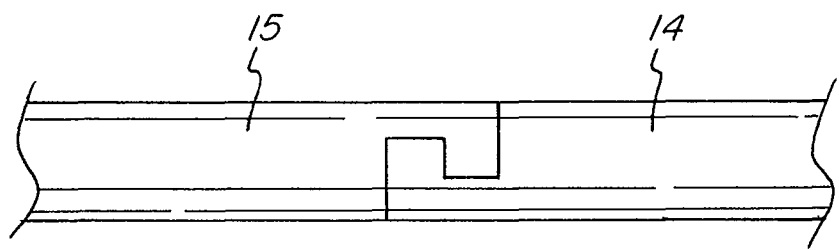
FIG. 10a shows in schematic longitudinal section a further illustrative embodiment of the connection elements of the proximal and distal portions of the transmission element when connected to each other.
Figure 10B:
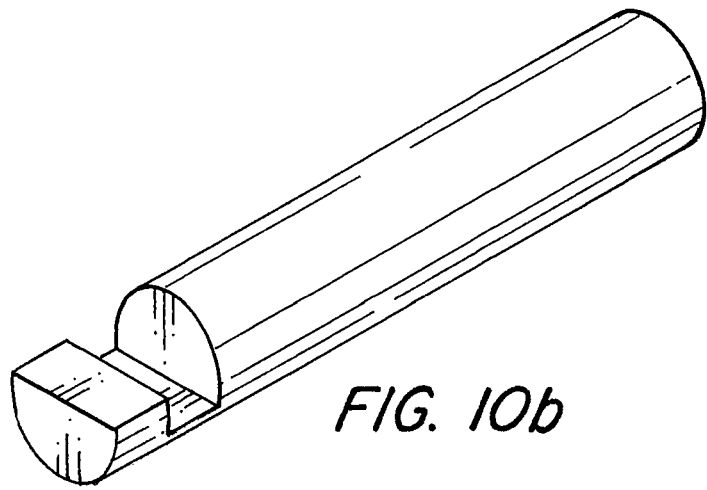

As is shown in FIGS. 10*a* and 10*b*, a connection can be created by a complementary form-fit design of the proximal end of the distal portion 15 with the distal end of the proximal portion 14 of the pull rod 13. The complementary connection elements of the distal portion 14 and of the proximal portion 14 of the pull rod 13 can be pushed laterally into each other and thereby connected to each other, and they can be separated from each other by lateral movement. If the pull rod 13 with the two connection elements is pushed into the proximal portion 3 of the outer shaft 2, such a lateral movement is blocked by a form fit and, in this way, release of the connection is safely prevented. The connection elements shown in FIGS. 10*a* and 10*b* are not axially symmetrical and thus allow the proximal portion 14 to be connected to the distal portion 15 of the pull rod 13 in a manner secure against twisting.

Figure 11:
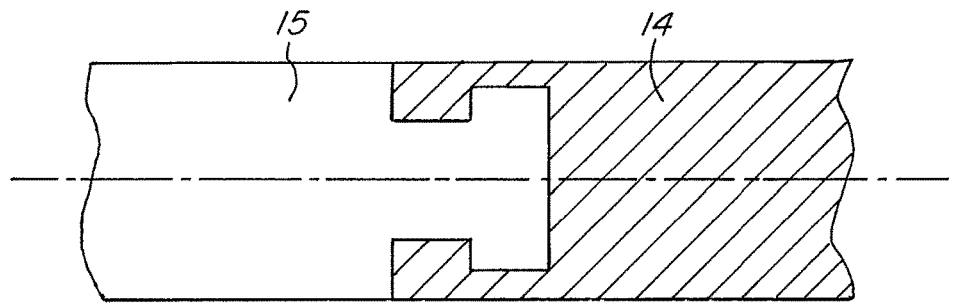
FIGS. 11 to 13 each show in longitudinal section three further illustrative embodiments of the connection elements of the proximal and distal portions of the transmission element when connected to each other.

A further form-fit design in which a connection is created by lateral insertion is shown in FIG. 11. These connection elements are also not rotationally symmetrical with respect to the longitudinal axis of the pull rod 13 and thus make it possible to prevent an axial twisting of the distal portion 15 relative to the proximal portion 14 of the pull rod 13.

Figure 12:
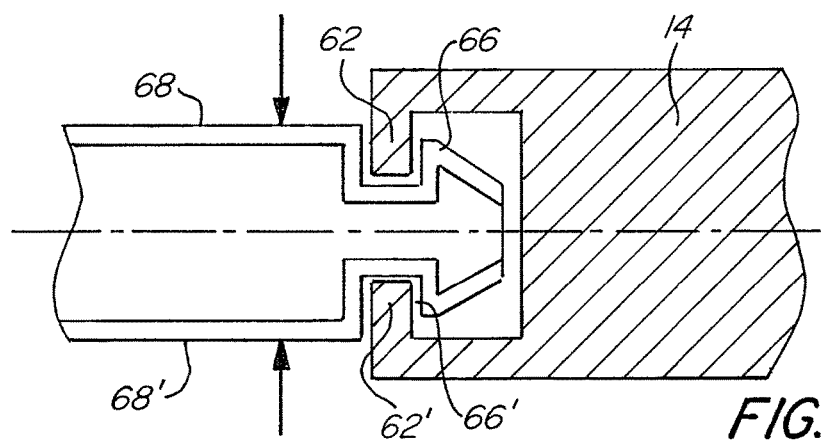

According to FIG. 12, a connection can be created by holding elements designed as elastically resilient barbs 66, 66' and arranged at the proximal end of the distal portion 15 of the pull rod 13, which holding elements engage with a form fit behind axially inwardly facing projections 67, 67' at the distal end of the proximal portion 14 of the pull rod 13. The connection can be easily produced by axial insertion of the barbs 66, 66' behind the projections 67, 67'. The connection can be separated again, as is indicated by the arrows in FIG. 12, by lateral compression of the resilient tabs 68, 68' that carry the barbs 66, 66'. The connection element formed by the tabs 68, 68' with the barbs 66, 66' can be designed in a simple manner as a slotted tube.

Figure 13:
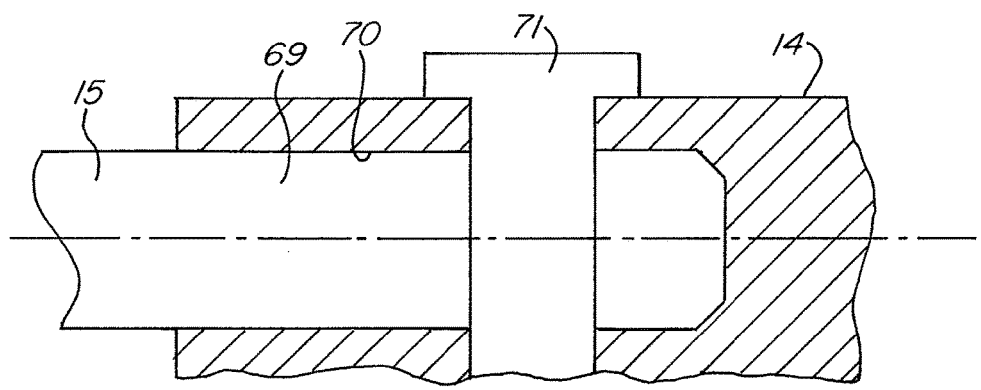

In a further embodiment of the connection elements as shown in FIG. 13, a cylindrical proximal end portion 69 of the distal portion 15 of the pull rod 13 can be pushed axially into a cylindrical blind hole 70 of the proximal portion 14 of the pull rod 13 and can be secured against withdrawal by a pin 71 that can be pushed in in the transverse direction. The pin 71 is secured against falling out by the proximal portion of the outer shaft 2 pushed over the proximal portion 14 of the pull rod 13. The pin 71 also secures the connection against twisting.

For the sake of clarity, not all reference signs are shown in all of the figures. Reference signs that are not explained in connection with one figure have the same meaning as in the other figures.

LIST OF REFERENCE SIGNS 1 shaft
2 outer shaft
3 proximal portion
4 distal portion
5 irrigation attachment
6 connection mechanism
7 sleeve
8 attachment nozzle
9 tab
10 stopper
11 tool
12, 12' scissor blade
13 pull rod
14 proximal portion
15 distal portion
16 ball
17 insulating sleeve
20 tube
21 shrink-on hose
22 insert
23 helix
25 tube
26 shrink-on hose
27 insert
28 helix
30 lever mechanism
31 distal end area
32 ball
33 pin
34 pin
35 slit
40 snap-fit mechanism
41, 41' jaw
42, 42' tab
43 bore
44, 44' slit
50 handle
51 coupling
52 rotary wheel
53 pivotable part
54 stationary part
55 attachment
56 push-button
60, 60' half-shells 61 plate
62, 62' hook
63 end portion
64 outer thread
65 inner thread
66, 66' barb
67, 67' projection
68, 68' tab
69 end portion
70 blind hole
71 pin

The invention claimed is:

1. A rigid endoscopic instrument, comprising:
a shaft having an outer shaft and a transmission element;
a tool arranged at a distal end of the shaft;
and a handle arranged at a proximal end of the shaft;
the outer shaft having a proximal portion and a distal portion connected releasably to each other by a first tubular helix on the proximal portion and a second tubular helix on the distal portion at a location approximately halfway between the proximal end of the shaft and the distal end of the shaft;
the transmission element having a proximal portion arranged movably inside the proximal portion of the outer shaft, and a distal portion arranged movably inside the distal portion of the outer shaft, the proximal portion of the transmission element and the distal portion of the transmission element being connected releasably to each other at a location approximately halfway between the proximal end of the shaft and the distal end of the shaft.

2. The instrument according to claim 1, wherein the tool is connected to a distal end of the distal portion of the transmission element by a lever mechanism.

3. The instrument according to claim 1, wherein the helix of the second connection element projects longitudinally beyond the proximal end of the distal portion of the outer shaft.

4. The instrument according to claim 1, wherein the tool and the handle are connected to the transmission element and to the outer shaft in such a way that the tool can be actuated by the handle by a movement of the transmission element relative to the outer shaft.

5. The instrument according to claim 1, wherein a length of the proximal portion of the outer shaft is approximately equal to a length of the distal portion of the outer shaft; and
wherein a sum of the length of the proximal portion of the outer shaft and the length of the distal portion of the outer shaft is approximately equal to a total length of the outer shaft.

6. The instrument according to claim 1, wherein the proximal portion and the distal portion of the transmission element each have a connection element for the form-fit releasable connection of the proximal portion to the distal portion of the transmission element.

7. The instrument according to claim 6, wherein the connection elements of the proximal portion and of the distal portion of the transmission element are connected to each other in such a way that, when the connection elements are arranged in the outer shaft, the proximal portion and the distal portion of the transmission element are connected non-releasably to each other.

8. The instrument according to claim 6, wherein the connection elements of the proximal portion and of the distal portion of the transmission element are designed for producing a snap-fit connection with one or more jaws or barbs mounted in an articulated or elastically resilient manner.

9. The instrument according to claim 6, wherein the connection elements of the proximal portion and of the distal portion of the transmission element are pushed into each other in a transverse direction.

10. The instrument according to claim 6, wherein the connection elements of the proximal portion and of the distal portion of the transmission element are connected to each other, and separated from each other, by rotation about the longitudinal axis of the transmission element.

11. The instrument according to claim 1, wherein the distal portion and the proximal portion of the transmission element are connected to each other in a manner secure against twisting, and in that the distal portion of the transmission element is connected or to the distal portion of the outer shaft in a manner secure against twisting, and the proximal portion of the transmission element is connected to the proximal portion of the outer shaft in a manner secure against twisting.

12. The instrument according to claim 11, wherein the proximal portion of the transmission element and the proximal portion of the outer shaft are connected to a handle in such a way that a connection secure against twisting is obtained between the proximal portion of the transmission element and the proximal portion of the outer shaft.

13. The instrument according to claim 1, wherein the instrument is an electrosurgical endoscopic instrument.

14. An endoscopic instrument, comprising:
an outer shaft having a first portion and a second portion;
the first portion of the outer shaft having an interior surface with a first tubular helix;
the second portion of the outer shaft having an exterior surface with a second tubular helix;
the second tubular helix engaged by the first tubular helix;
a transmission element arranged inside the outer shaft, the transmission shaft having a first portion and a second portion, the first portion of the transmission element connected to the second portion of the transmission element;
wherein the first tubular helix is arranged substantially between an inner surface of the first portion of the outer shaft and an outer surface of the first portion of the outer shaft;
and wherein the helix of the second portion of the outer shaft is arranged between an inner surface of the second portion of the outer shaft and an outer surface of the second portion of the outer shaft.

15. The instrument according to claim 14, wherein the first tubular helix and the second tubular helix are complementary cut-outs of a surface of a hollow cylinder having a diameter approximately equal to a diameter of the first portion of the outer shaft.

16. The instrument according to claim 14, wherein the first portion of the transmission element and the second portion of the transmission element are releasably connected by rotation about the longitudinal axis of the transmission element.

17. The instrument according to claim 16, wherein a rotation direction to release the first portion of the transmission element and the second portion of the transmission element is counter to a rotation direction to release the first tubular helix from the second tubular helix.

18. The instrument according to claim 15, wherein the interior surface with the first helix is inserted into the first portion of the outer shaft, and the exterior surface with the second helix is inserted into the second portion of the outer shaft.

* * * * *